United States Patent
White

[19]

[11] Patent Number: 6,134,967
[45] Date of Patent: Oct. 24, 2000

[54] DETECTION OF DELAMINATION OF RUBBER COVERS FROM METAL SUBSTRATES

[75] Inventor: Dennis A. White, St. George Island, Fla.

[73] Assignee: Beloit Technologies, Inc., Wilmington, Del.

[21] Appl. No.: 09/309,856

[22] Filed: May 11, 1999

[51] Int. Cl.$^7$ .................................................. G01N 29/00
[52] U.S. Cl. .............................. 73/588; 73/618; 73/633; 73/635
[58] Field of Search ............................ 73/579, 588, 596, 73/597, 598, 599, 600, 618, 632, 633, 635, 640

[56] References Cited

U.S. PATENT DOCUMENTS

| | | |
|---|---|---|
| 3,512,400 | 5/1970 | Lynnworth . |
| 3,918,296 | 11/1975 | Kitada . |
| 4,164,150 | 8/1979 | Ries et al. . |
| 4,576,048 | 3/1986 | Glenn . |
| 4,586,379 | 5/1986 | Burkhardt, Jr. . |
| 4,594,897 | 6/1986 | Bantz . |
| 4,699,007 | 10/1987 | Kawashima et al. . |
| 5,007,291 | 4/1991 | Walters et al. . |
| 5,329,561 | 7/1994 | Desruelles . |
| 5,492,012 | 2/1996 | Terhune . |
| 5,681,996 | 10/1997 | White . |
| 5,887,517 | 3/1999 | Liang et al. . |

OTHER PUBLICATIONS

"Extensions to Other Types of Surface Waves"—Part 3—pp. 42 to 44.
"Theory of Beam Divergence"—Ultrasonic Testing—p. 56.
"Testing for Regional Bond Integrity"—Ultrasonic Testing—pp. 662 to 664.
"Angle Beam Test of Metal/Composite Laminates"—Ultrasonic Testing—pp. 253–254.
"Leaky Lamb Waves"—Ultrasonic Testing—pp. 521 to 524.
"Auto–V System—Automated Thickness/Velocity Measurement System"—USN–52V Manual Supplement—Krautkramer.
"Standard Guide for Acousto—Ultrasonic Assessment of Composites, Laminates, and Bonded Joints"—ASTM—pp. 769 to 776.

*Primary Examiner*—Richard A. Moller
*Attorney, Agent, or Firm*—Lathrop & Clark LLP

[57] ABSTRACT

The bonding of an elastomeric cover to a metal roll is tested by transmitting audible frequency waves through the compliant roll cover and receiving the waves at a transducer mounted to the underlying steel roll. The resulting signal may be analyzed by a technician listing to the audio frequencies transmitted. The audio range of frequencies employed may be about 5000 Hz. The elastomeric material such as rubber does not transmit sound without considerable loss of amplitude, whereas sound travels at high speed through steel with little attenuation. A sound transmitter is spirally scanned along the rubber-covered surface of the roll, transmitting into the steel roll directly beneath the sound transmitter and throughout the roll. Sound is detected at a transducer mounted at the roll ends. Any failure or significant variation in the roll/cover bond is detected by the effect on the quality of sound transmitted through the rubber steel interface.

21 Claims, 2 Drawing Sheets

DETECTION OF DELAMINATION OF RUBBER COVERS FROM METAL SUBSTRATES

CROSS REFERENCES TO RELATED APPLICATIONS

STATEMENT AS TO RIGHTS TO INVENTIONS MADE UNDER FEDERALLY SPONSORED RESEARCH AND DEVELOPMENT

BACKGROUND OF THE INVENTION

The present invention relates to methods for testing bond integrity in general and apparatus employing sound waves to detect bond integrity in particular.

In papermaking and many other applications, a rubber or elastomeric coating is bonded to a metal roll, typically a steel roll. In many industrial applications, particular papermaking, a web of material is processed by passing it through a nip formed between a pair of opposed rolls. The width of the contact between the opposed rolls along the direction of motion of the web is referred to as the nip width. Without any compliance, a pair of opposed rolls meets only along a line of contact. Real materials such as steel, which have a high modulus of elasticity, have little or no nip width, and as a result can produce very high pressures within the nip. In many applications a wider nip with a lower pressure is desirable. A wider nip also results in the web passing through the nip having longer dwell time within the nip. Nip dwell time is proportional to nip width and inversely proportional to web speed. A compliant roll cover results in a wider nip. Nip widths of one-half to one inch or more can be achieved with compliant roll covers. Compliant roll covers are typically fabricated of synthetic rubber, or epoxy or other resin system which is sometimes reinforced with fabric.

The rubber, synthetic rubber, or other compliant material must be bonded to a supporting metal roll, typically a steel roll. Bonding is one industrial process in which it is difficult to verify has been properly performed. Careful control of the materials and process used in the bonding is often relied upon to assure quality. However, when new materials or processes are developed, it is highly desirable to be able to non-destructively determine bond integrity. Even with known bonding techniques, unknown variables can result in bonding problems from time to time, creating a need for a technique for detecting the quality of the bond formed between a metal roll and an elastomeric cover.

One known technique for monitoring bonding between an elastomeric cover and the underlying roll, is to tap/strike the bonded roll cover with a wooden stick and listen for changes in the sound produced. With experience a technician can obtain some indication of bond uniformity.

What is needed is an analytical method of detecting the quality of the bond between a roll and an elastic roll cover.

SUMMARY OF THE INVENTION

The testing method of this invention employs audible frequency waves which are transmitted through a compliant roll cover and received by a transducer mounted to the underlying steel support roll. The resulting signal may be analyzed by a technician listing to the audio frequencies transmitted. The resulting signal may alternatively be analyzed by a heterodyning circuit. The results from the heterodyning circuit may be converted to a voltage or processed through a fast Fourier transform and analyzed in the frequency domain. The audio range of frequencies employed may be, for example about 5,000–10,000 Hz. An elastomeric material has a relatively low modulus of elasticity thus transmitting sound less well than metal. Steel has a very high speed of sound, and sound travels with little attenuation through steel. A sound transmitter is scanned along the surface of an elastomeric-covered roll and the sound is transmitted into the steel roll directly beneath the sound transmitter and transmitted throughout the roll. Sound is detected at a sensor mounted at one or both roll ends. Any failure or significant variation in the bond between the roll cover and the roll is detected by the effect on the quality of sound transmitted through the rubber steel interface.

It is a feature of the present invention to provide an analytical method of detecting bond integrity between an elastomeric cover and a metal roll.

It is a further feature of the present invention to provide a method of generating a map indicative of bond quality between an elastomeric cover and a metal support roll.

It is another feature of the present invention to provide an apparatus for generating and recording a map indicative of the way sound is transmitted through the interface between an elastomeric cover and a metal support roll.

Further objects, features and advantages of the invention will be apparent from the following detailed description when taken in conjunction with the accompanying drawings.

DESCRIPTION OF THE PREFERRED EMBODIMENTS

Figure 1:
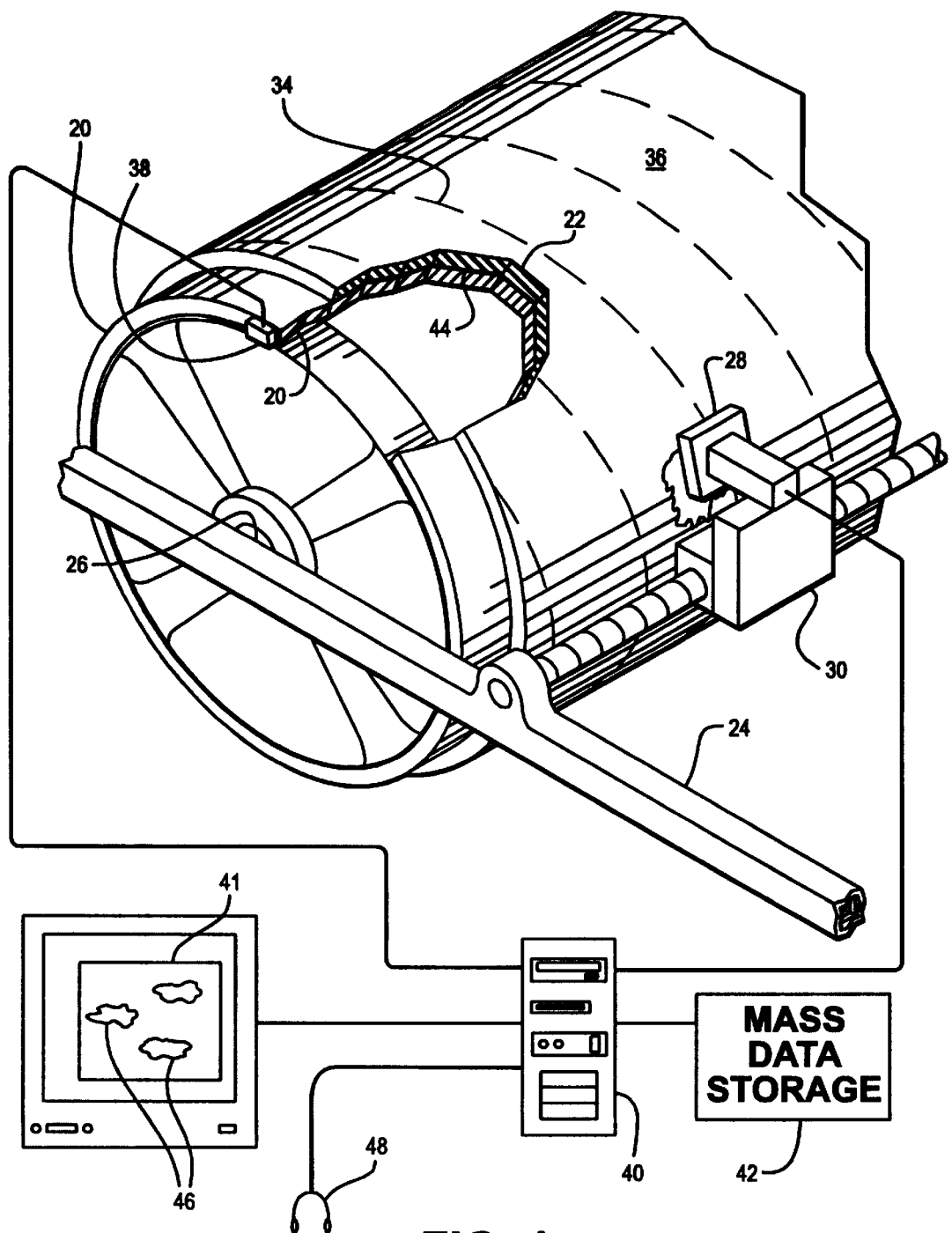
FIG. 1 is an isometric schematic view, partly cutaway, of apparatus of this invention for practicing a method of inspecting the bond between an elastomeric cover and a supporting metal roll.
Figure 2:
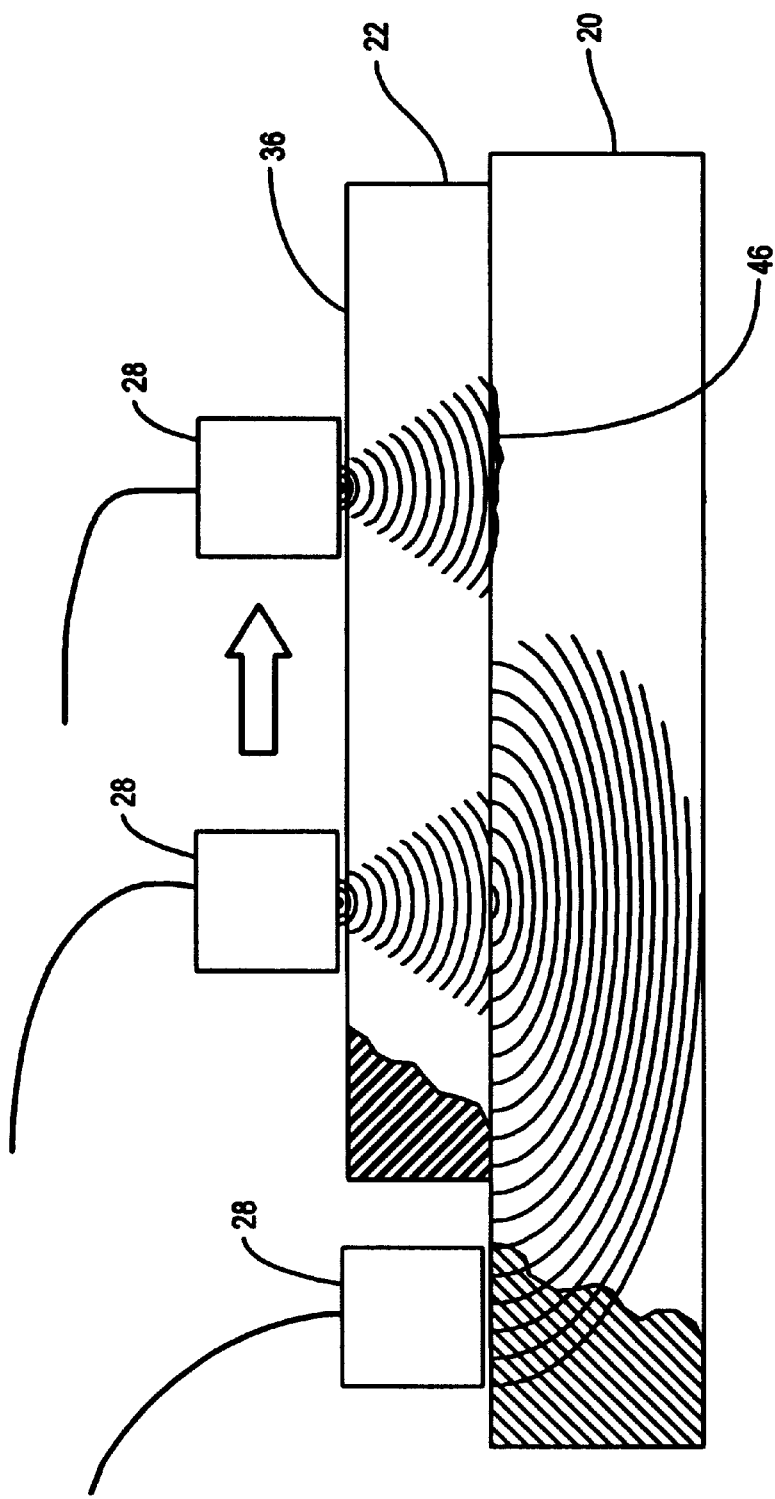
FIG. 2 is a side elevational schematic view illustrating the transmission of sound through the roll cover to detect bond integrity using the method of FIG. 1.

Referring more particularly to FIGS. 1–2, wherein like numbers refer to similar parts, a roll 20 which has a compliant or elastomeric cover 22 is mounted to a test fixture 24. The metal roll 20 is mounted for rotation by a bearing 26 to the test fixture 24. A sound transmitter 28 is mounted to a carriage 30 which is mounted to a lead screw 32. The carriage 30 traverses the axial length of the roll 20 as the roll is caused to turn. The rotation of the roll and the translation of the carriage 30 may be mechanically linked, in a manner well known to those skilled in the art, so that the sound transmitter 28 describes a spiral pattern 34 on the surface 36 of the cover 22 of the roll 20. Water or other coupling medium may be supplied between the sound transmitter 28 and the cover 22 to increase the coupling of sound between the transmitter 28 and the cover 22.

A sound receiving sensor 38 is mounted to the metal roll 20 and connected by radio, infrared, or through an electrical commutator (not shown) to a computer 40. The computer 40 may be a specialized instrument or a general purpose computer employing a data receiving board. The computer contains or is connected to a data storage system 42 which can store the results of an entire scan of the roll compliant surface 36. The data received from the transducer 38 may be processed to create a map 41 of the roll cover 22 showing one or more parameters related to the sound detected by the sound receiving transducer 38.

Transmission of sound is generally considered a compression wave which propagates through a medium at a speed proportional to the square root of the density and inversely proportional to the square root of the modulus of elasticity of the medium. Acoustical impedance, which is the total reaction of a medium to the transmission of sound through the medium, influences the transmission of sound between different mediums. Acoustical impedance is expressed as the ratio of sound pressure to particle velocity at a given point in a medium. Steel has an acoustical impedance of 45.94 kg/m^2/sec.; brass has an acoustical impedance of 36.64; synthetic rubber has an acoustical impedance of about 1.59; and air has an acoustical impedance of about 1.18. When sound waves penetrate the rubber cover 22, as shown in FIG. 2, they propagate downwardly until they reach the interface 44 between the cover 22 and the metal roll 20. The change in acoustical impedance of sound between the rubber cover 22 and the metal, or steel, roll 20 causes a significant amount of the sound not to pass through the interface 44. If a defect 46 in the bond between the cover 22 and the roll 20 exists, as shown in FIG. 2, the sound waves propagating through the roll cover meet air or vacuum which, having substantially lower impedances than steel, results in the interrogating sound being completely or nearly complete reflected.

Once sound penetrates from the roll cover 22 into the steel roll 20, the sound propagates rapidly and efficiently throughout the steel roll 20, reaching the sound receiving transducer 38. Rubber or any elastomeric material is not a very good sound conductor because of its low modulus of elasticity and acoustical impedance. Moreover, sound which does not propagate directly to the metal roll reaches the interface 44 at an angle which, due to additional travel distance through the rubber coating, is attenuated. Furthermore, beyond an angle governed by Snell's law, sound is reflected at the interface 44, so very little sound which does not propagate directly downwardly from the sound transmitter 28 is transmitted to the steel roll. The result is that the sound detected by the receiving transducer 38 is a good indicator of the bond quality between the roll 20 and the cover 22 directly beneath the sound transmitter 28.

A typical sound transmitter 28 may have a diameter of about one inch and the lead screw may be designed to cause the spiral path to spiral out 0.9 inches between rotations of the roll 20.

The output of the receiving transducer 38 may be analyzed in a number of different ways. The simplest is to simply listen to the amplified output of the transducer 38 on a speaker (not shown) or headphones 48 to detect a sound level or some qualitative change.

More sophisticated approaches are to analyze the received signal and map various signal parameters to a specific location on the roll 20. To aid in mapping a signal output to a particular location on the roll 20, position encoders (not shown) on the roll and the carriage 30, which carries the transmitter 28, will normally be employed. A witness mark (not shown) from which the scanning is initiated may also be employed to allow matching of data from one scan to another.

The signal received by the transducer 38 can be analyzed for amplitude and the amplitude corrected for the distance between the transmitter 28 and the transducer 38, as determined analytically or empirically. Adjusted signal amplitude should directly correspond to bond quality. The shape of the transmitted wave form may be analyzed or the frequency distribution resulting from transmission and perhaps induced frequency shifts may be analyzed. A fast Fourier transform may be performed on the transducer 38 output to analyze the frequency distribution of the transmitted signal.

A sensitive system for detecting frequency shifts is a heterodyne analyzer, in which the electric signal from the transducer 38 beats with a signal from an oscillator and one of the side bands produced by this modulation is then passed through a fixed filter and detected.

An experimental test was performed utilizing ultrasonic equipment in which an ultrasonic transmitter was pulsing at sonic frequencies and the sonic pulses which were detected after passing through the roll cover into the supporting roll, were found to vary in frequency when roll cover bond integrity varied.

The experiment involved utilizing a 200-kHz ultrasonic transducer which was driven on and off to form a square wave about 10 kHz. An ultrasonic receiver having a range of 60 to 300 kHz was mounted to the end of the steel roll on which the rubber cover was bonded. An audio signal was detected from the amplified output of the ultrasonic receiver, this audio signal shifted in audible quality/frequency, when the ultrasonic transducer was moved over the roll cover surface, the detectable quality/frequency change was apparently related to bond quality between the roll cover and the roll immediately beneath the ultrasonic transducer. The following equipment was utilized in conducting the experiment:

SENSING UNIT

Krautkramer USN52 UT system, with 200 KHz (resonant in steel) UT transducer, pulse repetition rate=(high) 10,000 Hz See http://www.krautkramer.com/products/products.htm

RECEIVING UNIT

Physical Acoustics Corp. 3104 module (100–300 KHz filter), with R6I sensor (peak resonance at 60 KHz) http://www.pacndt.com/Welcome.html The experiment is interpreted as verifying the concept of detecting roll cover bond quality by transmitting audio sound through the rubber cover into the underlying steel support roll and monitoring the transmitted signal. The experiment may represent an alternative embodiment of the invention providing particular utility where an audio frequency is used to modulate an ultrasonic carrier. The use of an ultrasonic carrier signal may facilitate utilizing an ultrasonic receiver and may produce a signal which has different or even advantageous properties in terms of detecting bond integrity.

Paper is manufactured in widths of up to 400 inches which means rolls used to handle a paper web may have lengths of more than 33 feet. The maximum length of steel through which sound must propagate from a transmitter supplying sound through the center of a rubber covering is thus about 17 feet.

It should be understood that although a spiral scanning system is described, any mechanical system which systematically scans the surface of the roll cover could be used. This would include indexing systems and robotic arm systems, thus generally covering any combination of translation and rotation of the sound transmitter 28 and/or the roll 20 and cover 22 bonded thereto.

It should be understood that the sound receiving transducer is a sensor sensitive to sound waves which is fixedly mounted during the scanning of the roll cover surface. The sensor will typically be mounted to the underlying steel roll where it is accessible typically at roll ends. It could be mounted to a roll head if the head or other structure is in good acoustical connection with the underlying roll.

Roll covers are typically applied to an underlying steel, cast iron, or brass roll which has been grit blasted, and degreased, the cover material may then be extruded and spirally wrapped onto the roll. Following extrusion onto the prepared roll surface, the roll is often vulcanized, then turned and ground to final dimensions. The roll cover must be an elastomeric material which here refers to rubber, both natural and synthetic including polyurethanes, and other plastic materials which include epoxy, and phenolic which have significantly lower moduluses of elasticity then steel and allow some compliance in the roll. The thickness of such materials is typically one-half to one and one-half inches thick.

It is understood that the invention is not limited to the particular construction and arrangement of parts herein illustrated and described, but embraces such modified forms thereof as come within the scope of the following claims.

I claim:

1. A method of detecting variations in bond quality between a metal roll and an elastomeric cover, comprising the steps of:

moving a sound generating source along an outer surface of an elastomeric roll cover, thereby causing sound waves to travel from the moving sound generating source through the elastomeric cover, and through a bond between the elastomeric cover, and into an underlying metal roll;

detecting the sound waves with a sensor fixedly mounted to the metal roll; and analyzing the detected sound waves for variations as the sound source is moved over the surface of the elastomeric cover.

2. The method of claim 1 wherein the variation analyzed is sound amplitude.

3. The method of claim 1 further comprising the step of storing a value corresponding to at least one parameter produced by the analyzing of the detected sound waves for a multiplicity of positions of the sound generating source as it is moved along the outer surface of the elastomeric roll cover.

4. The method of claim 3 further comprising the step of displaying a map correlating the at least one parameter to physical positions on the roll cover.

5. The method of claim 1 wherein the variation analyzed is the shape of the sound waves.

6. The method of claim 1 wherein the variation analyzed is the frequency of the sound waves.

7. The method of claim 1 wherein the step of moving the sound generating source includes employing a mechanical system which systematically scans substantially all of the surface of the roll cover.

8. The method of claim 1 wherein the sound generating source employs sound in the audio frequency range.

9. The method of claim 8 wherein the sound generating source employs sound in the frequency range between 1,000 Hz and 10,000 Hz.

10. The method of claim 1 wherein the sound generating source employs ultrasonic sound which is modulated with an audio wave.

11. The method of claim 10 wherein the ultrasonic sound has a frequency of approximately 200 kHz and the modulated acoustic wave has a frequency of approximately 10 kHz.

12. An apparatus for inspecting the bond between an elastomeric roll cover and a metal roll comprising:

a sound generating source;

a metal roll adapted for use in a papermaking machine, the roll having an elastomeric cover bonded thereto, the elastomeric cover having an outwardly facing surface;

a means for systematically scanning the sound generating source over substantially all of the surface of the roll cover;

a sensor fixedly mounted to the metal roll;

a computer in data receiving relation with the sensor;

a data storage means connected to the computer to receive data corresponding to the output of the sensor.

13. The apparatus of claim 12 further comprising a means for converting the output of the sensor to a voltage.

14. The apparatus of claim 12 further comprising a display connected to the computer for displaying a map of the roll cover bond showing at least one parameter relating to data received from the sensor.

15. A method of detecting variations in bond quality between a metal roll and an elastomeric cover, comprising the steps of:

moving a ultrasonic sound generating source which is pulsed at a audio frequency along an outer surface of an elastomeric roll cover;

causing sound waves to travel from the ultrasonic sound generating source through the elastomeric cover, and through a bond between the elastomeric cover, and into an underlying metal roll;

detecting the sonic pulsed waves with an ultrasonic sensor fixedly mounted to the metal roll; and analyzing the detected ultrasonic sound waves for variations in the audio frequency as the ultrasonic sound source is moved over the surface of the elastomeric cover.

16. The method of claim 15 wherein the variation analyzed is amplitude.

17. The method of claim 15 further comprising the step of storing a value corresponding to at least one parameter produced by the analyzing of the detected ultrasonic sound waves for a multiplicity of positions of the sound generating source as it is moved along the outer surface of the elastomeric roll cover.

18. The method of claim 15 further comprising the step of displaying a map correlating the at least one parameter to physical positions on the roll cover.

19. The method of claim 15 wherein the variation analyzed is the frequency of the audio pulses.

20. The method of claim 15 wherein the step of moving the ultrasonic sound generating source includes employing a mechanical system which systematically scans substantially all of the surface of the roll cover.

21. The method of claim 15 wherein the ultrasonic sound has a frequency of approximately 200 kHz and the modulated acoustic pulse has a frequency of approximately 10 kHz.

* * * * *